(12) United States Patent
Hager, III et al.

(10) Patent No.: US 6,819,121 B1
(45) Date of Patent: Nov. 16, 2004

(54) METHOD AND APPARATUS FOR MEASUREMENT OF CONCRETE CURE STATUS

(75) Inventors: Nathaniel E. Hager, III, Lancaster, PA (US); Roman Domszy, Lancaster, PA (US)

(73) Assignee: Material Sensing & Instrumentation, Inc., Lancaster, PA (US)

( * ) Notice: Subject to any disclaimer, the term of this patent is extended or adjusted under 35 U.S.C. 154(b) by 76 days.

(21) Appl. No.: 10/278,660

(22) Filed: Oct. 23, 2002

(51) Int. Cl.[7] .......................... G01R 27/26; G01N 27/00
(52) U.S. Cl. ...................... 324/664; 324/71.7; 324/676
(58) Field of Search ........................ 324/71.7, 664, 324/676, 643, 658, 663, 679, 686, 693, 705

(56) References Cited

U.S. PATENT DOCUMENTS

| | | | |
|---|---|---|---|
| 4,769,601 A | 9/1988 | Herrick | 324/300 |
| 5,136,249 A | 8/1992 | White et al. | 324/643 |
| 5,748,002 A * | 5/1998 | Scott et al. | 324/633 |
| 5,872,447 A * | 2/1999 | Hager, III | 324/71.1 |
| 6,281,801 B1 * | 8/2001 | Cherry et al. | 340/605 |
| 6,396,265 B1 | 5/2002 | Shtakelberg et al. | 324/300 |

OTHER PUBLICATIONS

Time–Domain Reflectometry of Water Content in Portland Cement, Nov. 1997, Charles J. Korhonen et al Special Report 97–27 U.S. Army Corps of Engineers, Cold Regions Research & Engineering Laboratory.

Microwave Dielectric Study of Water Structure in the Hydration Process of Cement Paste, vol. 81 No. 1, pp 213–216 Journal of the American Ceramic Society, (1999) Nobuhiro Miura et al.

* cited by examiner

*Primary Examiner*—Anjan Deb
*Assistant Examiner*—Donald M Lair
(74) *Attorney, Agent, or Firm*—Martin Fruitman

(57) ABSTRACT

An apparatus and a method for determining the cure state of thermosetting concrete using time domain reflectometry. A miniature capacitor is constructed at the end of a coaxial transmission line which is immersed in the curing concrete so that the concrete is the dielectric of the capacitor, and step function voltage pulses are fed to the transmission line, while the reflected signal from the line is monitored. The amplitude at several points of the reflected pulses, which are related to the free water and bound water in the concrete and indicate the degree of cure, are fed to a computer for interpretation and display.

13 Claims, 5 Drawing Sheets

METHOD AND APPARATUS FOR MEASUREMENT OF CONCRETE CURE STATUS

BACKGROUND OF THE INVENTION

This invention deals generally with electrical measuring and testing, and more specifically with the determination of the non-electric property of the state of cure of concrete by the use of time domain reflectometry.

The degree of cure of concrete is of vital interest in the construction industry because the cure status determines the strength and degree of shrinkage of a concrete structure and therefore whether it can be subjected to subsequent construction processes. However, since the cure status of the internal portion of a concrete structure can not be evaluated visually, considerable effort has been expended to find methods to accurately evaluate the cure state concrete.

Several electrical methods to determine the cure state of concrete have been used. Among them are spin-echo nuclear magnetic resonance (U.S. Pat. No. 6,396,265 to Shtakelberg et al) and pulsed nuclear magnetic resonance spectrometry (U.S. Pat. No. 4,769,601 to Herrick). Miura et al have also performed laboratory tests (published in the Journal of the American Ceramic Society, Vol. 81, No. 1, pp 213–216) on the use of time domain reflectometry to evaluate the degree of concrete cure. However, Miura used a surface probe and took no measurements within the interior of any structures. Furthermore, the measurements were so widely separated in time, that the tests yielded little more than information the conditions of the initial and final states of the concrete.

SUMMARY OF THE INVENTION

The present invention has demonstrated a time domain reflectometry apparatus which furnishes highly accurate and very repeatable measurements of the free-water, bound-water, and ion-conductivity components of the chemical state of the curing concrete. The change in the relationships of these chemical states over a very wide frequency range can be used to closely follow the curing status of the concrete. The invention combines the simplicity of electrical sensing with miniaturization available from high frequency techniques in a time domain reflectometry measuring device. Furthermore, calibration readings have been established for many concrete mixes with specific additives, so that the apparatus is usable for in-situ monitoring of the cure status of most types of concrete.

The frequency spectrum of time delay reflectometry pulses in curing concrete separates into three easily identifiable components. One is the free water response representing water in the unattached state measured at the higher frequencies above 1 GHz. This quantity falls during the cure period. The second component is the bound water state representing water attaching to the developing microstructure, measures at the mid-frequencies between about 1 MHz and 1 GHz, the quantity of which increases during the cure. The third identifiable component is the ion conductivity, measured at the lover frequencies between about 10 kHz and 1 MHz, representing ions moving through the microstructure, which decrease during the cure.

Although it is feasible to observe these changes by transforming the data into a microwave frequency spectrum for scientific-quality analysis, direct interpretation in the time domain is far more useful for field use. A further benefit of the invention is that when the measurements are performed in the time domain, sensor response can be separated from other effects by propagation delay.

The invention is thereby very beneficial for overcoming quality control problems, increasing construction speed, and improving the uniformity of the concrete, especially in critical structures.

In the preferred embodiment of the invention, a sensor embedded within the structure being constructed receives and reflects a fast rise time pulse, and the reflected transient signal occurring in the microwave frequency range relates to the water states for any particular concrete mix. Because of this phenomenon, the reflected signal can be directly related to free and bound water states and percent of cure. In experimental tests, changes in the signal have been followed during processing and compared to other test methods to establish information in regard to the relationship of the reflected signal to the free and bound water states and to the state of cure.

The sensor is a miniature capacitor constructed at the end of a semi-rigid coaxial transmission line that is immersed in the curing concrete. Step function voltage pulses are fed to the transmission line, and the reflected signal from the transmission line is monitored. The amplitudes of the reflected pulse signals, which are related to the free water response, and the decay characteristics of the reflected pulse signals, which are related to the bound water, are then fed to a computer for interpretation and comparison to previously secured standards.

The invention thereby furnishes a real time measurement of the state of cure of the concrete, and the transmission line and sensor, which remain in place after the material is cured, can actually be used with the same signal generator and signal processing system to later check for cracks or discontinuities which might develop in the cured concrete at a later time.

DETAILED DESCRIPTION OF THE INVENTION

Figure 1:
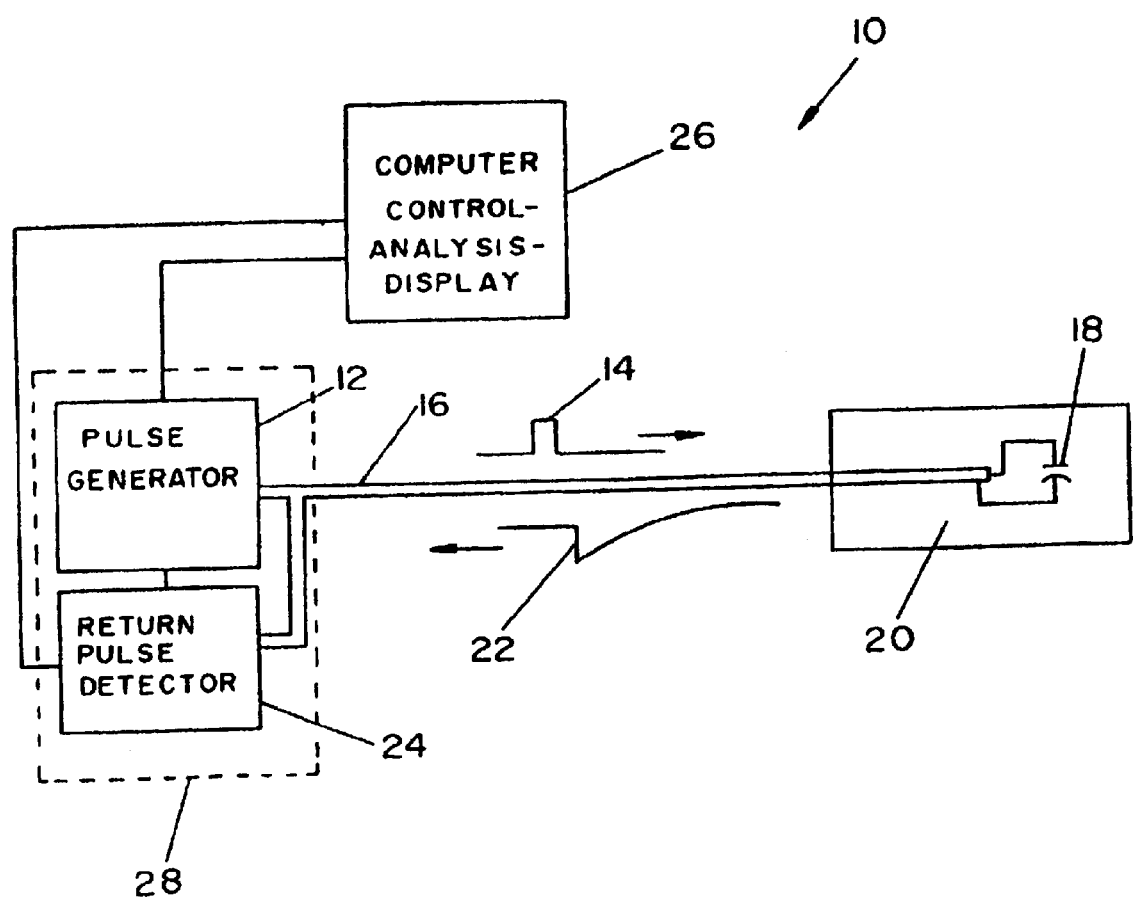
FIG. 1 is a simplified schematic diagram of the preferred embodiment of the apparatus of the invention.

FIG. 1 is a simplified schematic diagram of the preferred embodiment of cure monitoring apparatus 10 of the invention in which pulse generator 12 supplies step function incident pulse 14 to transmission line 16. Capacitor sensor 18 which is located at the remote end of transmission line 16, is immersed within curing concrete 20 and reflects return pulse 22 back to pulse detector 24. The timing of pulse generator 12, the analysis of return pulse 22, and the display of the test parameters and results are performed by computer 26.

The parameters of the reflected pulse which indicate the cure status of the concrete are the variations in the amplitude over time at various points along the pulse waveform. These are affected by the several states of the water within the concrete. Changes in the reflected pulse parameters are actually indications of a more sophisticated change in frequency characteristics of the concrete, so that measurements of the changing characteristics of the reflected pulse actually measure changes in the material's frequency characteristics.

The frequency characteristics can also be measured by direct application of by computer 26 of a signal sweeping through a wide spectrum of frequencies and spectrum analysis by computer 26 of the returning signals, but such an arrangement is more difficult to measure. The pulse technique used in the preferred embodiment of the invention uses a fast risetime pulse of a few nanoseconds or less, which is well understood in the art to actually include a wide spectrum of frequencies. The reflected pulse then actually includes the desired frequency information, and a Laplace Transform can also be used to arrive at the complex permittivity. However, the desired information of cure status can also be secured by making simple measurements on the reflected pulse.

The invention's preferred embodiment of a method of measuring cure status is:

A) immersing at least one end of a transmission line into concrete which is curing, with a capacitor connected to the immersed end of the transmission line, and the capacitor constructed so that its dielectric is the concrete into which it is immersed;

B) generating one or more step function voltage pulses and feeding the pulses to the transmission line;

C) receiving reflected pulses back from the capacitor at the end of the transmission line; and D) analyzing changing characteristics of the reflected pulses to establish the water states and status of cure of the concrete in which the transmission line is immersed.

In most installations, pulse generator 12 and pulse detector 24 are actually included in one unit, sampling head 28. In the preferred embodiment sampling head 28 is an Algilent Technologies model 54754A Time Domain Reflectometry Sampling head which has a 35 picosecond input transient and a 20 GHz detection bandwidth.

In the preferred embodiment, incident pulse 14 is 200 millivolts, with a rise time of 35 picoseconds. The pulse length and repetition rate are not critical as long as the pulse length is long enough and the repetition rate is slow enough so that they do not result in additional pulses being generated during the 1 to 10 microseconds after the beginning of the reflected pulse when pulse analysis is being performed. The desirable pulse risetime and detector sampling resolution is in the range of 1 picosecond to 100 picoseconds. Pulses can also be produced in bursts to produce a lower effective frequency so that data is transferred to computer 26 at a lower effective rate.

Transmission line 16 can be any type of controlled impedance high frequency transmission line. As described in regard to FIG. 2, the preferred embodiment uses coaxial cable transmission line. For the preferred embodiment, 3.5 mm, 50 ohm, semi-rigid coaxial cable is used. The length of transmission line 16 is 1 to 2 meters and the specific length is chosen to avoid ¼ wave reflections. The line itself must be free of connectors which would add undesirable signal distortions and reflections.

Figure 2:
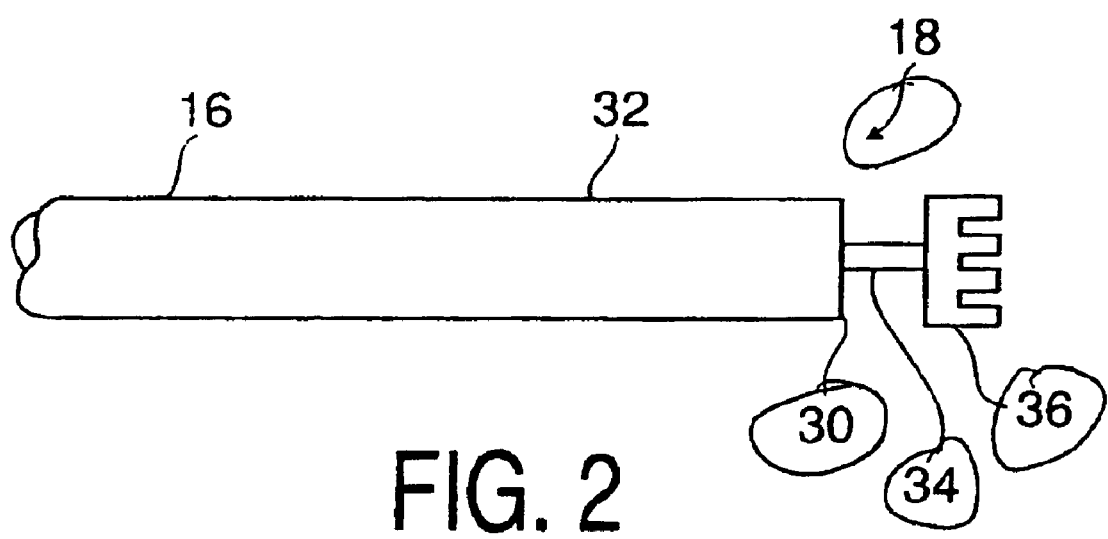
FIG. 2 is a side view of the sensor and a short length of the transmission line of the preferred embodiment of the apparatus of the invention.

Sensor 18, which is immersed in setting concrete 20, is essentially a miniature capacitor whose fringing electric field extends into the concrete and changes the reflection at the end of transmission line 16 as the permittivity of the concrete changes. In the preferred embodiment sensor 18 is a 0.05 to 0.1 picofarad capacitance formed near the end of transmission line 16, as shown in FIG. 2, but it is practical to use a capacitance in the range between 0.03 and 10 picofarads. Sensors must be physically small, since wavelengths at the highest frequencies are of the order of millimeters. At 10 GHz the free space wavelength is 30 mm, which reduces to 34 mm in high permittivity water. This produces a quarter wavelength of 1 mm or less, and care must be used in sensor design to avoid quarter-wavelength resonance in free water.

FIG. 2 is a side view of sensor 18 and a short length of transmission line 16 of the preferred embodiment of the apparatus of the invention. Because of the very small dimensions involved, FIG. 2 is not a scale drawing. Sensor 18 is located at end 30 of cable 16, which is a 3.5 mm diameter semi-rigid coaxial line such as the Micro-Coax UT-141. Sensor 18 is formed as a short section of inner conductor 34 protruding from end 30 of cable 16 by removing outer conductor 32 and the inner teflon insulating sleeve (not shown) to expose only inner conductor 34. Inner conductor 34 is trimmed, by filing while viewing it with a microscope, to between 0.01 mm and 1.5 mm. The exact length is determined by calibration against known standards such as acetone with a permittivity of 21.1 or acetonitrile with a permittivity of 37.5.

Since the exposed tip of inner conductor 34 is an effective radiator in high permittivity liquids, it must be shielded to prevent radiation and distortion of the reflected signal. This is accomplished with serrated shield 36, which provides a surrounding ground to propagating modes while allowing free flow of concrete through the sensor 18. A 4.0 by 0.7 mm castle nut works well as serrated shield 36 with the particular transmission cable of the preferred embodiment, and the nut can be twisted onto inner conductor 34 with the serrations extending away from transmission line 16 and parallel to inner conductor 34. This structure eliminates radiating fields and allows an evanescent near field in the area around the tip to yield an ultra-high frequency capacitance measurement rather than an antenna measurement.

Figure 3:
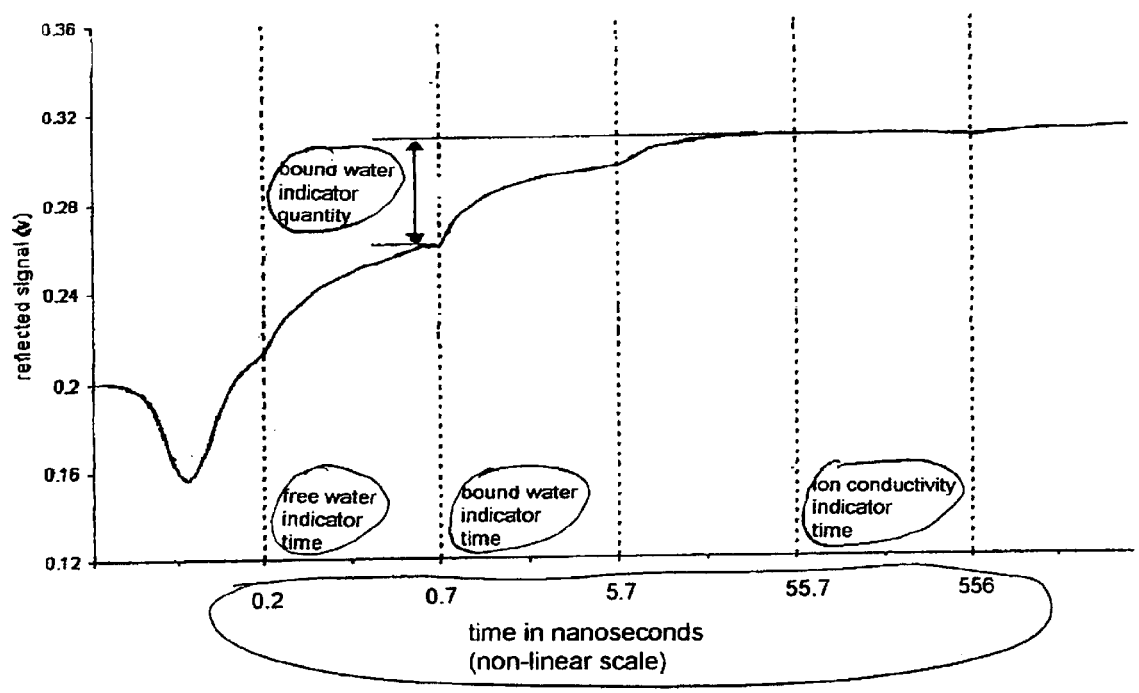
FIG. 3 is a graph of a typical time domain reflected pulse indicating the three points in time after the pulse begins at which typical readings are taken.

FIG. 3 is a graph of a typical time domain reflected pulse about 48 hours into the cure indicating the three points in time at which readings are taken in the preferred embodiment of the invention. The readings taken at 200 picoseconds are an indicator of the status of free water within the concrete, and the long term change in this reading is pictured in FIG. 4. The readings at 0.7 nanoseconds are subtracted from the readings at 55 nanoseconds to secure the graph of the long term change in the indicator for bound water that is shown in FIG. 5.

The bound water indicator could also be generated by using the 200 picosecond readings alone, without subtracting the ion conductivity reading at 55 nanoseconds. However, the reading at 200 picoseconds includes both the bound water and the ion conductivity factors, so this subtraction of the amplitudes of the pulse at widely varying times is made in order to make the variations of bound water with cure time more apparent. The result also generates a better indicator of the history of the cure at the various times, which is valuable to know because it affects the final strength and can be used to show the effects of retarders and accelerators.

The actual subtraction of the two readings on each reflected pulse can be accomplished automatically by the Agilent Technologies model 54754A Time Domain Reflectometry Sampling head of the equipment used in the preferred embodiment of the invention shown in FIG. 1, or by any conventional computer programmed to perform the subtraction.

Figure 4:
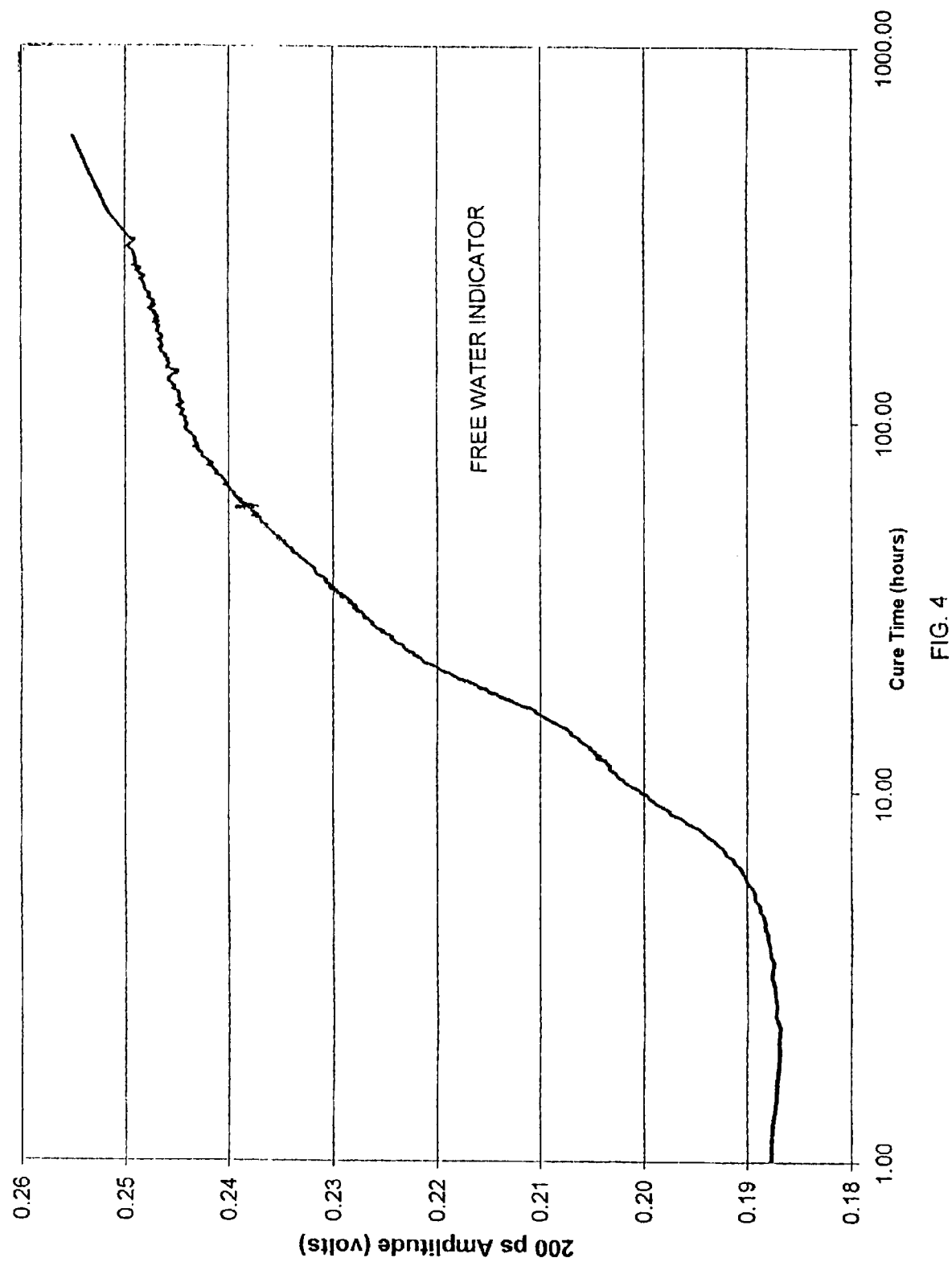
FIG. 4 is a graph of a typical free water indicator showing the variation in the amplitude of the reflected pulse at 200 picoseconds after the pulse begins, plotted against the time of the concrete cure on a logarithmic scale.
Figure 5:
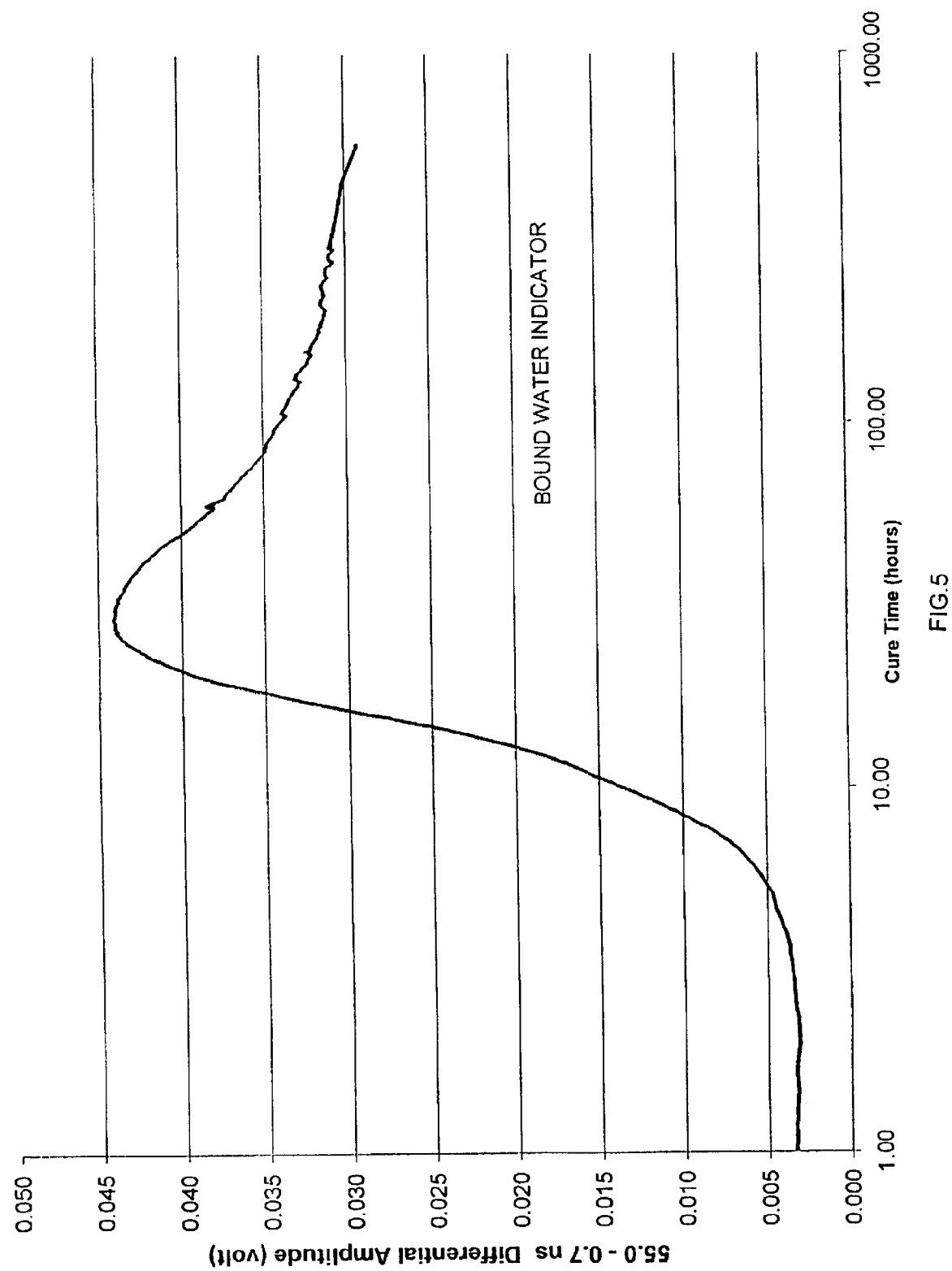
FIG. 5 is a graph of the typical bound water indicator showing the variation in the amplitude of the reflected pulse at 55 nanoseconds after the pulse begins minus the amplitude of the reflected pulse at 0.7 nanoseconds after the pulse begins, plotted against the time of the concrete cure on a logarithmic scale.

FIG. 4 is a graph of the typical free water indicator, which, in the preferred embodiment, is the variation in the amplitude of the reflected pulse at 200 picoseconds after the pulse begins, plotted against the time of the concrete cure on a logarithmic scale. This parameter represents the 10 GHz behavior that contains the free water response, and is inversely related to the quantity of free water in the concrete, so that the measured voltage at this 200 picosecond point increases as the free water decreases.

FIG. 5 is a graph of the typical bound water indicator which is the variation in the amplitude of the reflected pulse at 55 nanoseconds after the pulse begins minus the amplitude of the reflected pulse at 0.7 nanoseconds after the pulse begins, plotted against the time of the concrete cure on a logarithmic scale. These readings represent the 20 MHz behavior showing the bound water response and increase to a peak at about 20 hours of the cure time. These readings then begin to fall as the water becomes more tightly bound and the time delay reflectometry frequency spectrum broadens.

Both FIG. 4 and FIG. 5 are graphs of readings taken on Portland cement with an initial water content of 40 percent. Such graphs can be generated for any variation of concrete components, and have been produced in a laboratory for high alkali cement, low alkali cement, Portland cement with sodium gluconate retarder, and tricalcium silicate, which is the primary constituent of Portland cement. With such data available to computer 26 of FIG. 1, it is a simple task to establish when a concrete has experienced equivalent signal changes and therefore to establish the state of cure by comparing the changing characteristics of the reflected pulses to characteristics of pulses reflected during previous controlled tests of curing concretes. This is easily accomplished by the use of computer 26 whose memory can include the previous test results. Moreover, controlled tests can be run and put into memory for any new type concrete so that later production testing equipment can evaluate such new materials.

However, previous test results are not a necessity. An alternate method of analysis is to measure and compare the changing amplitudes at either of two points of the pulse for a series of reflected pulses over a relatively long period of time, in effect creating a graph similar to either FIG. 4 or FIG. 5 for a particular cement. As indicated in FIGS. 4 and 5, typically, one of these observation points on the reflected pulses is less than 1 nanosecond after the reflected signals begin, and the other observation point on the reflected pulses is greater than 25 nanoseconds after the reflected pulses begin. Such graphs will display curves similar to FIGS. 4 and 5 and will indicate the state of the concrete's cure regardless of the time scale on the graph.

The electronic parameter readings by the invention have been verified in the laboratory by comparison against physical tests for cure characteristics of the concrete, such as standard tests for weight loss when free water is removed. Such tests have shown excellent agreement between the method of the invention and elaborate and destructive laboratory tests.

The present invention thereby provides an accurate and reliable means to evaluate cure status of various concretes, and is capable of performing the task in either the laboratory or the production environment.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims.

For example, shapes other than a serrated shield can be used to terminate inner conductor 34 of capacitor 18. Moreover, as indicated in the text, amplitude readings can be taken at various points on the reflected pulse.

What is claimed as new and for which Letters Patent of the United States are desired to be secured is:

1. A method of measuring the status of cure of concrete comprising:

immersing at least one end of a transmission line into concrete which is curing, with a capacitor connected to the immersed end of the transmission line, and the capacitor constructed so that the dielectric of the capacitor is the concrete into which the capacitor is immersed;

generating one or more step function voltage pulses and feeding the pulses to the transmission line;

receiving reflected pulses back from the capacitor at the end of the transmission line; and analyzing changing characteristics of the reflected pulses to establish the water states and status of cure of the concrete in which the transmission line is immersed.

2. The method of claim 1 wherein analyzing the reflected pulse comprises comparing characteristics of the reflected pulse to characteristics of pulses reflected during previous tests of curing concrete.

3. The method of claim 1 further including generating a series of pulses and analyzing the reflected pulses by comparing the changing amplitudes of the reflected pulses over time to determine the status of cure of the concrete.

4. The method of claim 1 further including generating a series of pulses and analyzing the reflected pulses by comparing the changing amplitudes at various times along the reflected pulses over time to determine the status of cure of the concrete.

5. The method of claim 1 further including transforming the reflected pulse into the frequency domain and analyzing the resulting frequency spectrum to determine the status of cure of the concrete.

6. The method of claim 1 wherein analyzing the reflected pulse comprises comparing over time the amplitudes of the reflected pulses at a point on the reflected pulses which is less than 1 nanosecond after the reflected pulses begin.

7. The method of claim 1 wherein analyzing the reflected pulse comprises comparing over time the amplitudes of the reflected pulses at a point on the reflected pulses which is greater than 25 nanoseconds after the reflected pulses begin.

8. An apparatus for measuring the status of cure of concrete comprising:

a pulse generator generating at least one step function voltage pulse;

a transmission line connected to and receiving pulses from the pulse generator, with one end of the transmission line immersed in concrete which is curing;

a capacitor connected to the immersed end of the transmission line and also immersed in the concrete which is curing, the capacitor being constructed so that the dielectric of the capacitor is the concrete into which it is immersed;

a pulse detector connected to the transmission line and receiving a signal from the transmission line which is a pulse reflected from the immersed capacitor; and an analyzer means interconnected with the pulse detector, the analyzer means being capable of measuring the changes in reflected pulses as the state of water within the concrete changes.

9. The apparatus of claim 8 wherein the pulse generator and the pulse detector are included in the same instrument.

10. The apparatus of claim 8 wherein the transmission line is coaxial, with an inner conductor, an insulator, and an outer conductor, and the capacitor is integrated into the transmission line by removing outer conductor and the inner insulating sleeve of the cable to expose only the inner conductor trimmed to a range of between 0.01 mm and 1.5 mm of length.

11. The apparatus of claim 10 further including a shield attached to the end of the inner conductor.

12. The apparatus of claim 10 further including a serrated shield attached to the end of the inner conductor.

13. The apparatus of claim 8 wherein the capacitance of the capacitor is in the range of between 0.03 and 10 picofarads.

* * * * *